(12) United States Patent
Gollar, III et al.

(10) Patent No.: US 7,060,652 B2
(45) Date of Patent: Jun. 13, 2006

(54) GAS SENSOR

(75) Inventors: Edward L. Gollar, III, Cincinnati, OH (US); Joseph R. Stetter, Hayward, CA (US); Nathan Schattke, Yorkville, IL (US)

(73) Assignees: OmegaPoint Systems, LLC, Cincinnati, OH (US); Transducer Technology, Inc., Newark, CA (US)

( * ) Notice: Subject to any disclaimer, the term of this patent is extended or adjusted under 35 U.S.C. 154(b) by 0 days.

(21) Appl. No.: 11/274,214

(22) Filed: Nov. 15, 2005

(65) Prior Publication Data

US 2006/0062694 A1 Mar. 23, 2006

Related U.S. Application Data

(62) Division of application No. 10/779,263, filed on Feb. 13, 2004.

(51) Int. Cl.
*B01J 21/08* (2006.01)
*B01J 21/12* (2006.01)
*B01J 21/14* (2006.01)
*B32B 5/02* (2006.01)
*B32B 27/04* (2006.01)

(52) U.S. Cl. .................. 502/261; 422/56; 422/83; 422/88; 422/98; 436/149; 436/150; 436/151; 436/152; 73/1.01; 73/1.02; 73/23.2; 502/100; 502/101; 502/229; 502/257; 502/258; 502/262; 502/325; 252/62.2; 204/430; 204/250

(58) Field of Classification Search ............... 502/100, 502/101, 229, 257, 261, 258, 262, 325; 422/56, 422/83, 88, 98; 73/1.01, 1.02, 23.2; 252/62.2; 204/430, 250
See application file for complete search history.

(56) References Cited

U.S. PATENT DOCUMENTS 4,058,482 A * 11/1977 Baris et al. .................. 502/101
4,150,076 A *  4/1979 Baris et al. .................. 264/49

* cited by examiner

*Primary Examiner*—Jill Warden
*Assistant Examiner*—Brian Sines
(74) *Attorney, Agent, or Firm*—Dinsmore & Shohl LLP

(57) ABSTRACT

A liquid electrode mixture for use in a gas sensor having from about 60 to about 240 milligrams of platinum black catalyst; from about 900 to about 1100 milligrams of water; from about 300 to about 400 microliters of 1-propanol; and from about 100 microliters to about 150 microliters of a polymer mixture comprising from about 40% to about 80% PTFE by weight and water.

2 Claims, 3 Drawing Sheets

GAS SENSOR

RELATED APPLICATIONS

The present application is a Divisional of U.S. application Ser. No. 10/779,263 filed Feb. 13, 2004. The entire disclosure of which is hereby incorporated by reference.

FIELD OF THE INVENTION

The present invention is directed to a gas sensor used to detect the presence of gases, such as ethanol.

BACKGROUND OF THE INVENTION

Many commercially available gas sensors are of the amperometric type having two or more electrodes in which a catalytically active metal is fixed to a porous substrate. The porous substrate may operate as a gas permeable membrane and structural support for the electrode. The electrodes are located on the inside surface of the membrane where they make contact with an electrolyte such as sulfuric acid. External circuitry maintains one of the electrodes, the working electrode, at a selected electrical potential with respect to one of the other electrodes during operation.

When the gas of interest diffuses through the porous membrane to reach the working electrode, the diffused gas is oxidized or reduced at the interface of the working electrode and the electrolyte. That reaction generates an electrical current that is proportional to the concentration of the gas. In some cases, the gas of interest reacts with another chemical which, in turn, is oxidized or reduced at the electrode. In some cases, sensors are of a galvanic design wherein a metal such as lead is oxidized to provide the opposite current to that occurring at the working electrode.

In amperometric ethanol sensors in the prior art, a large platinum black electrode has been needed to form a stable signal, making the sensor bulky and difficult to miniaturize. In addition, the need for a large amount of noble metal for the electrode made the sensor expensive.

Also in the prior art, the sensors were connected to the external circuit through wires. For example, a platinum contact wire was connected to the catalytically active electrode and passed through the sensor body to an external contact. Since most sensors contain a corrosive, liquid electrolyte, a difficulty with sensors has been providing secure electrical contact with the electrodes while maintaining an electrolyte-tight seal at the location where the conductor passes through the sensor body. In the prior art, seals around conductors have included Teflon gaskets. In other methods, the seal has been made of thermoplastic material or epoxy resin.

U.S. Pat. No. 5,744,697 to Martell, et al. discloses a gas sensor of the type described above. The Martell, et al. gas sensor has a plastic housing comprised of a plurality of conductive housing portions integrally formed with a plurality of non-conductive housing portions. The housing has a receptacle disposed therein, and a gas-sensing agent is provided in the receptacle. A support sheet that has a plurality of electrodes formed thereon is disposed above the receptacle wherein electrical contact is made with electrodes to the conductive plastic portion, and a wick disposed in the receptacle causes the gas-sensing agent to maintain electrolytically conductive contact with the electrodes formed on the support sheet inside the sensor assembly.

The present invention uses electrodes that are in electrical contact with conductive plastic portions, as in the Martell, et al. patent, but in a design that uses simpler electrode and sensor housing construction. This results in a smaller sensor that is less expensive to manufacture, easier to interface to external circuitry, and less prone to leaking.

SUMMARY OF THE INVENTION

The invention comprises a gas sensor assembly having a housing with a receptacle formed therein. The housing has non-conductive housing portions and conductive housing portions, each of which is physically and electrically isolated from the other, with the conductive housing portions being comprised of a conductive plastic material. A gas-sensing agent is disposed in the receptacle, and a plurality of electrodes are disposed in conductive contact with the gas-sensing agent and the conductive housing portions.

In one embodiment of the invention, the gas sensor assembly comprises a bottom conductive layer, a middle non-conductive layer,. and a top conductive layer. The receptacle is formed by an opening through the middle and top layers, with the bottom layer being solid with no opening. The bottom electrode, also known as the counter electrode, is in physical contact with the bottom conductive layer, with its active surface facing up towards the receptacle opening. The top electrode, also known as the working electrode, is in physical contact with the top conductive layer, with its active surface facing down towards the receptacle opening. A gas-sensing agent is disposed in the receptacle. Conductive wires are in physical contact with each conductive layer (and not in direct contact with the electrode surfaces) in order to facilitate connection to an external circuit.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

Figure 1:
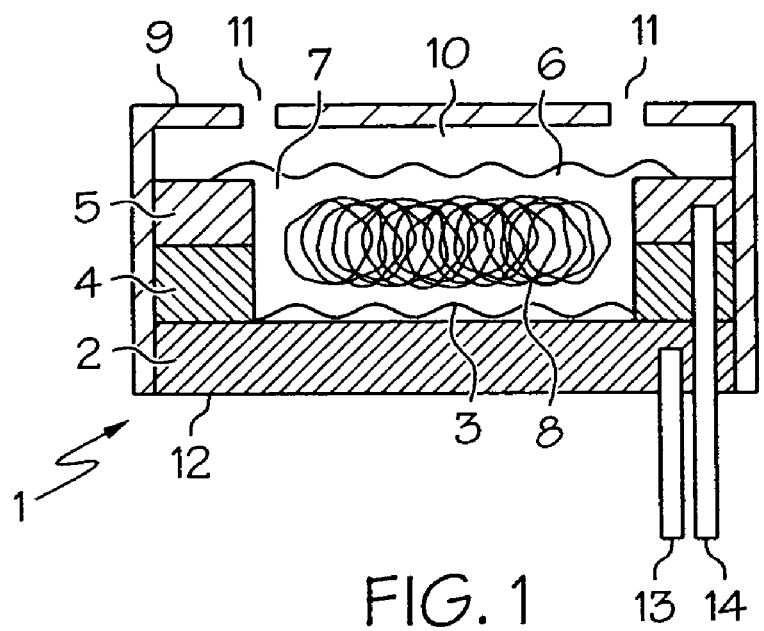
FIG. 1 is a schematic illustration of a cross-sectional view of an exemplary sensor assembly of the present invention.

The embodiments set forth in the drawings are illustrative in nature and not intended to be limiting of the invention defined by the claims. Moreover, individual features of the drawings and the invention will be more fully apparent and understood in view of the detailed description.

DETAILED DESCRIPTION OF THE INVENTION

Reference will now be made in detail to various embodiments of the invention, examples of which are illustrated in the accompanying drawings, wherein like numerals indicate similar elements through the views.

One exemplary embodiment of the gas sensor 1 in accordance with the invention is illustrated in FIG. 1 in a cross-sectional view. The sensor core 12 comprises the bottom portion 2, which could be a solid rectangular piece of conductive plastic. A rectangular electrode 3, also known as the counter electrode, is sized to fit within the cylindrical receptacle 7. Electrode 3 is in physical and electrical contact with the bottom portion 2, with its active surface facing upwards towards the cylindrical receptacle 7. The middle portion 4 of the sensor is in direct contact with the bottom portion 2 and is comprised of non-conductive plastic with a round center opening that forms the lower side walls of the receptacle 7. The middle portion 4 also serves to electrically insulate the lower portion 2 from the upper portion 5. The upper portion 5 of the sensor is in direct contact with the middle portion 4 and is comprised of conductive plastic with a round center opening that forms the upper side walls of the receptacle 7. A rectangular electrode 6, also known as the working electrode, is in physical and electrical contact with the upper portion 5, with its active surface facing downwards towards the receptacle 7. The receptacle 7 is filled with wick material 8 and with a gas sensing agent (not shown). The wick material 8 maintains electrode 3 in fluid contact with electrode 6. Wire 13 is in electrical contact with bottom portion 2 only and wire 14 is in electrical contact with upper portion 5 only. Wires 13 and 14 bring the electrical signal of sensor 1 to an external circuit (not shown). A cover 9 comprised of non-conductive plastic is fitted tightly over sensor core 12. Cover 9 forms a cavity 10 above the electrode 6. Holes 11 in the cover 9 allow the gas to be sensed to pass into and out of the cavity 10 and across the surface of electrode 6.

Typically, a sensor of this type would require a seal between each electrode (3 and 6) and its associated conductive portion (2 and 5, respectively). In this invention, the counter electrode 3 is fully contained within the body of the gas sensor, so there is no potential for there to be a leak of the gas-sensing agent from electrode 3 to the outside of the sensor body. This results in a two-electrode gas sensor with only one electrode sealing area that has the potential for leaks, thus increasing the reliability of the sensor.

Figure 2:
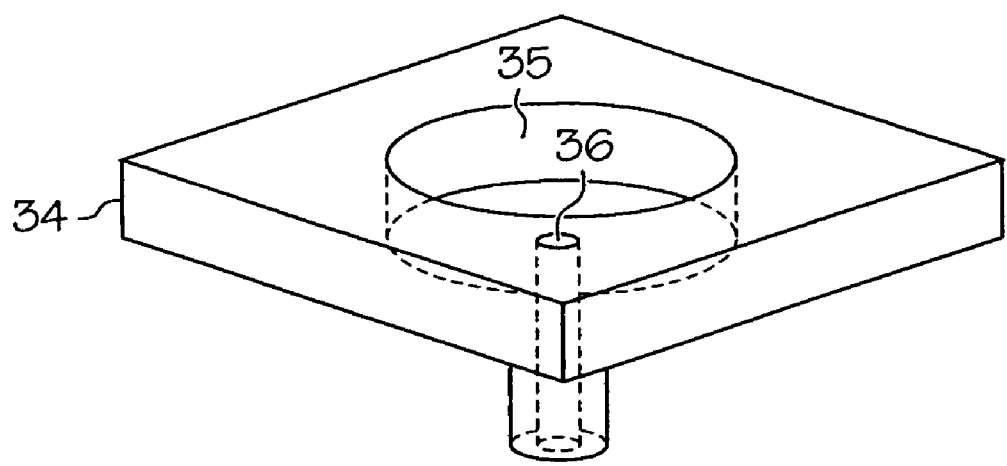
FIG. 2 is a schematic illustration of an exemplary sensor assembly of the present invention.

Core 12 may be formed of non-conductive plastic by injection molding machinery using a two step process with two molds. FIG. 2 illustrates the middle portion 34 that is formed in the first mold in the first step of the process. Middle portion 34 is rectangular in shape and has a circular opening 35 that serves as part of the receptacle 7. Middle portion 34 also has an opening 36 to allow for subsequent insertion of wire 14. In the second step of the process, wire 13 is first inserted into the second mold, middle portion 34 is next inserted, and wire 14 is finally inserted by passing it through opening 36. Upper portion 5 and lower portion 2 of core 12 are then molded with conductive plastic around portion 34 and wires 13 and 14. As a result, wire 13 will be in electrical contact with electrode 3 through lower portion 2, and wire 14 will be in electrical contact with electrode 6 through upper portion 5.

Figure 3:
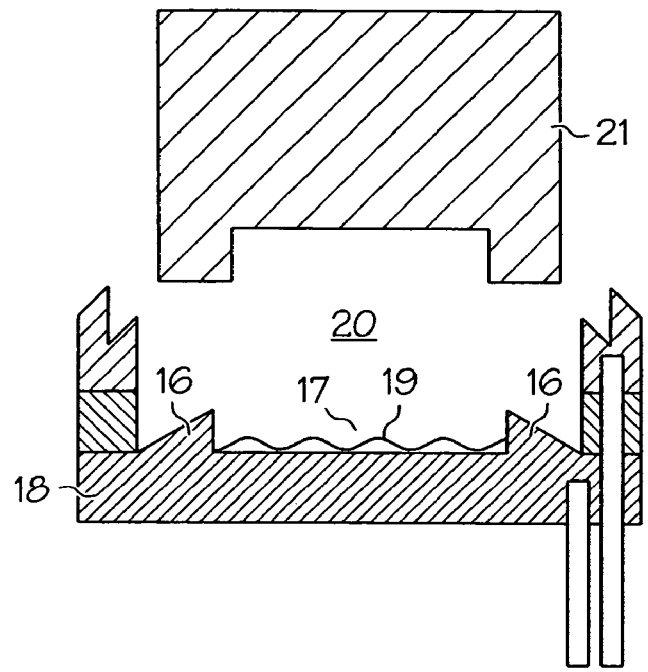
FIG. 3 is a schematic illustration of a cross-sectional view of an exemplary sensor core of the present invention depicting the bottom electrode heat welding process.

FIG. 3 is a cross sectional view of the sensor core 12 and is used to illustrate the first step that may be used in the fabrication of the sensor 1. The projections 16 are part of the conductive plastic portion 18 and form the rectangular cavity 17. The rectangular electrode 19 is placed within the cavity 17 with its active surface facing upwards toward cylindrical receptacle 20. A heated metallic cylinder 21 as is used in heat welding equipment is lowered into receptacle 20 and makes contact only with extensions 16. Extensions 16 are melted down and flow over top of the active surface of electrode 19, thus causing the surface of electrode 19 to be in electrical contact with portion 18.

Figure 4:
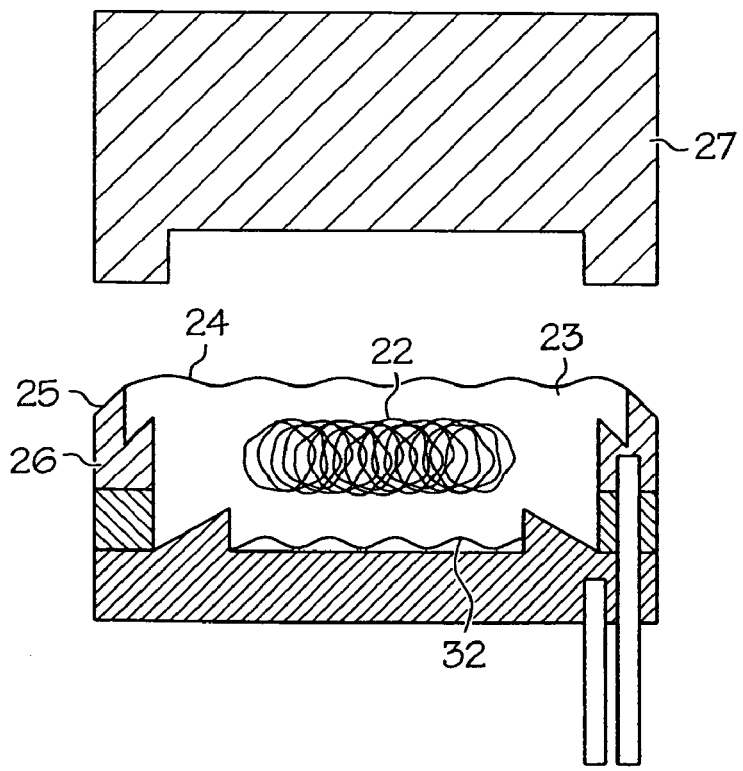
FIG. 4 is a schematic illustration of a cross-sectional view of an exemplary sensor core of the present invention depicting the top electrode heat welding process.

FIG. 4 is a cross sectional view of the sensor core 12 and is used to illustrate the next step that may be used in the fabrication of the sensor 1. Wick material 22 is placed within cylindrical receptacle 23. Edge 25 is circular in shape and forms the upper boundary of receptacle 23. Electrode 24 is rectangular in shape and is placed onto edge 25 of upper portion 26 with its active surface facing in towards the receptacle 23. A heated metallic cylinder 27 as is used in heat welding equipment is lowered onto electrode 24 and melts the edge 25 into the electrode 24, creating electrical contact and a liquid-tight seal between the electrode 24 and the upper portion 26.

Figure 5:
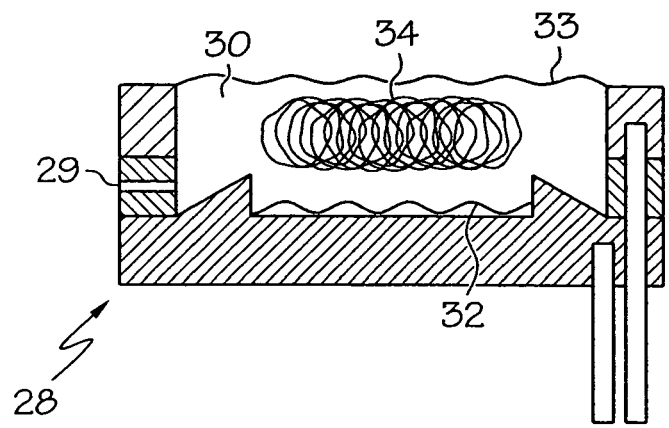
FIG. 5 is a schematic illustration of an exemplary sensor core of the present invention.

Referring to FIG. 5, the hole 29 forms a passageway from the outside surface of the core 28 to the receptacle 30. A gas sensing agent (not shown) is dispensed into receptacle 30 through the hole 29. The hole 29 may be sealed by applying heat to the outside surface of core 28 at the hole opening, melting plastic over the hole 29 causing a liquid-tight seal. The cover 9 may then be fitted over the core 28 to complete the sensor assembly.

Figure 6:
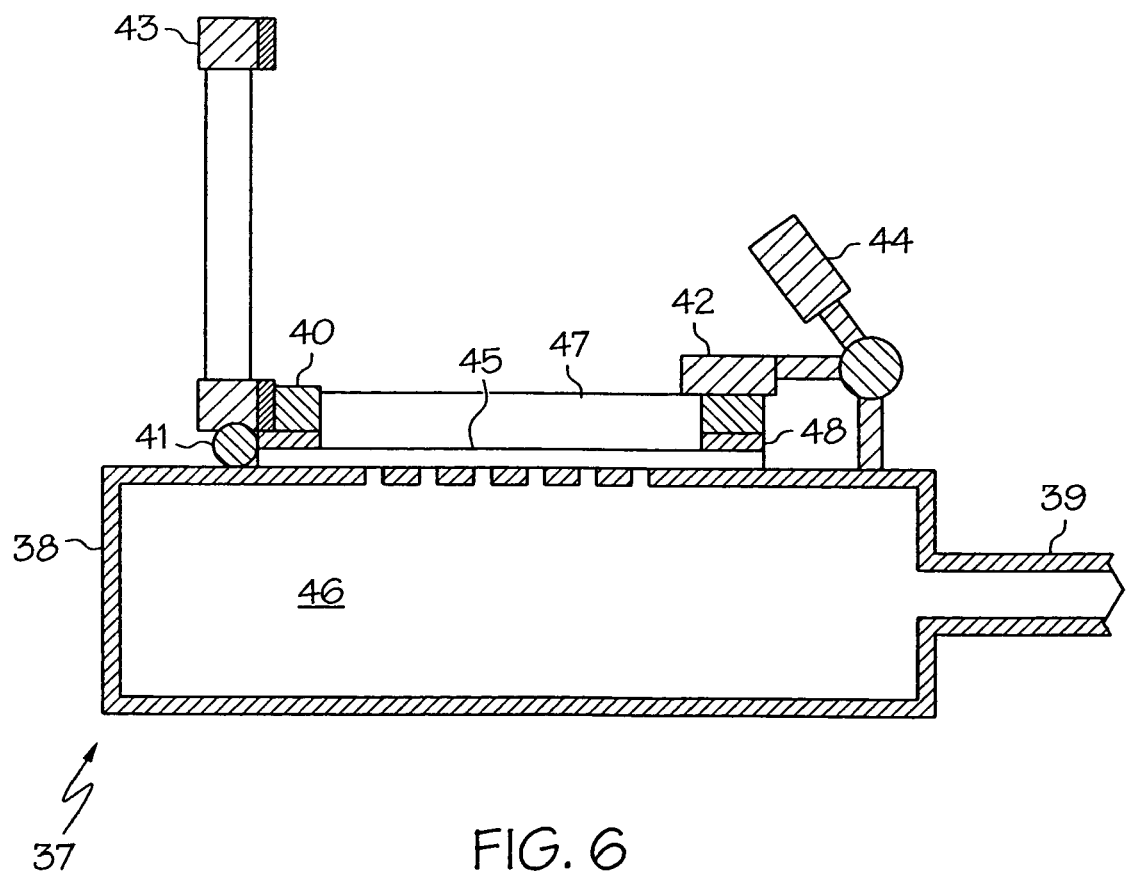
FIG. 6 is a schematic illustration of an exemplary apparatus to fabricate electrodes.

One exemplary way to fabricate the electrodes 3 and 6 is by using the apparatus 37 illustrated in FIG. 6, shown in cross-sectional view. The vacuum chamber 38 is connected to a valve and a vacuum source (neither shown) by way of the passageway 39. The rectangular plate 40 is connected to the vacuum chamber 38 with a hinge 41 along one edge. A foam gasket 48 is attached to the bottom edge of the plate 40. The clamp 42 is attached to the vacuum chamber 38 and when in the closed position holds the plate 40 securely to the vacuum chamber 38. Plate 40 and clamp 42 are shown in the closed position, and plate 43 and clamp 44 are shown in the open position. The electrode support sheet 45 is placed between the foam gasket 48 and the top surface of the vacuum chamber 38, and is held in place by the plate 40 and the clamp 42. The electrode support sheet 45 may be fabricated from porous Teflon (PTFE), which may be part number PM23JSF commercially available from MuPore, that is approximately 1.75 inches square and 0.010 inches thick. The electrode support sheet 45 may alternatively be made of any other porous non-reactive thermoplastic, such as polypropylene, polyethylene, or a combination of the two. The top area of the vacuum chamber 38 that is immediately underneath the frame 40 contains holes that allow for the passage of liquids from the area 47 above the electrode support sheet into the interior 46 of the vacuum chamber 38.

Another embodiment of the present invention comprises the a method to form the liquid electrode mixture. The method comprises: combining from about 60 to about 240 milligrams (preferably about 120 milligrams) of platinum black catalyst (e.g., fuel cell grade platinum black, part number S3002 commercially available from Englehard) with from about 900 milligrams to about 1100 milligrams (preferably about 1000 milligrams) of water and from about 300 microliters to about 400 microliters (preferably about 350 microliters) of 1-propanol (high purity grade). In one exemplary embodiment, the water comprises Type II 18 megaohm deionized water. The water, platinum black and 1-propanol are mixed together with a blender or mixer on high speed for about 3 to about 15 minutes (preferably about 5 minutes) or until evenly mixed.

About 200 to about 250 microliters (preferably 225 microliters) of 60% PTFE by weight (commercially available as PTFE 30 from DuPont) is mixed with about 8 to about 12 grams (preferably about 10 grams) of water. About 100 to about 150 microliters (preferably about 125 microliters) of the resulting solution is added to the water, platinum black and 1-propanol mixture described above. The combined mixture and solution is then mixed for about 2 to about 5 (preferably 3) more minutes.

A vacuum is applied to the vacuum chamber 38 and the electrode support sheet 45 is pre-wet with 1-propanol. The vacuum is maintained until the electrode support sheet 45 is clear. The vacuum is then stopped for 1 to 5 minutes. The liquid electrode mixture is then applied with a pipette to the electrode support sheet 45. A vacuum is then applied to the vacuum chamber 38 for approximately one minute, sucking the liquid electrode mixture through the electrode support sheet 45, leaving the catalyst material on top.

The electrode support sheet 45 is removed from the apparatus 37. It may then be cut into individual electrodes using a steel rule die, or by other means, with electrode 3 being 0.250 inches square, and electrode 6 being 0.500 inches square.

The foregoing description of the various embodiments of the invention has been presented for the purposes of illustration and description. It is not intended to be exhaustive or limit the invention to the precise form disclosed. Many alternatives, modifications, and variations will be apparent to those skilled in the art of the above teaching. Accordingly, this invention is intended to embrace all alternatives, modifications, and variations that have been discussed herein, and others that fall within the spirit and broad scope of the claims.

What is claimed is:

1. A liquid electrode mixture for use in a gas sensor, comprising:
   from about 60 to about 240 milligrams of platinum black catalyst;
   from about 900 to about 1100 milligrams of water;
   from about 300 to about 400 microliters of 1-propanol; and
   from about 100 microliters to about 150 microliters of a polymer mixture comprising from about 40% to about 80% PTFE by weight and water.

2. The liquid electrode mixture of claim 1, further comprising one or more surfactants, emollients, or flocculants.

* * * * *